US012654037B2

(12) United States Patent
Rus Carlborg et al.

(10) Patent No.: US 12,654,037 B2
(45) Date of Patent: Jun. 16, 2026

(54) MEDICAL APPARATUS FOR THE NON-INVASIVE TRANSMISSION OF FOCUSED SHEAR WAVES TO IMPACT CELLULAR BEHAVIOUR

(71) Applicant: Universidad De Granada, Granada (ES)

(72) Inventors: Guillermo Rus Carlborg, Granada (ES); Juan Antonio Marchal Corrales, Granada (ES); Juan Soler Vizcaino, Granada (ES); Juan Manuel Melchor Rodriguez, Granada (ES); Antonio Manuel Callejas Zafra, Granada (ES); Miguel Riveiro Taboada, Granada (ES); Gema Jimenez Gonzalez, Granada (ES); Ralph Sinkus, Clichy (ES)

( * ) Notice: Subject to any disclaimer, the term of this patent is extended or adjusted under 35 U.S.C. 154(b) by 0 days.

(21) Appl. No.: 18/021,096

(22) PCT Filed: Aug. 16, 2021

(86) PCT No.: PCT/EP2021/072706
§ 371 (c)(1),
(2) Date: Feb. 13, 2023

(87) PCT Pub. No.: WO2022/034237
PCT Pub. Date: Feb. 17, 2022

(65) Prior Publication Data
US 2023/0347181 A1 Nov. 2, 2023

(30) Foreign Application Priority Data
Aug. 14, 2020 (EP) ..................................... 20382752

(51) Int. Cl.
*A61N 7/00* (2006.01)

(52) U.S. Cl.
CPC ........ *A61N 7/00* (2013.01); *A61N 2007/0034* (2013.01)

(58) Field of Classification Search
CPC .............. A61N 7/00; A61N 2007/0034; A61N 2007/006; A61N 7/02; A61B 34/10; A61B 2090/374; A61P 17/00
See application file for complete search history.

(56) References Cited

U.S. PATENT DOCUMENTS

| | | | |
|---|---|---|---|
| 5,150,711 A * | 9/1992 | Dory ........................ | A61N 7/02 601/3 |
| 2004/0049134 A1 * | 3/2004 | Tosaya ............... | A61H 23/0236 601/2 |

(Continued)

FOREIGN PATENT DOCUMENTS

WO 2016020572 2/2016

OTHER PUBLICATIONS

Reddy, J.N. "A Study of Conservation Principles with Applications", Principles of Continuum Mechanics, Cambridge University Press, 2010, pp. 1-246.

(Continued)

*Primary Examiner* — Pascal M Bui Pho
*Assistant Examiner* — Michael Yiming Fang
(74) *Attorney, Agent, or Firm* — McCarter & English, LLC

(57) ABSTRACT

The present invention refers to a medical apparatus that allows to generate, non-invasively and at a requested depth shear waves of controlled frequency and amplitude. The purpose is to impact via mechanotransduction on cellular behavior, i.e. cell proliferation and cell migration. The aim is to aide classical tumor therapy for instance by rendering (Continued)

cells more receptive to drugs, or by gaining time during chemotherapy by reducing cell migration and hence slowing down the metastatic process.

7 Claims, 8 Drawing Sheets

(56)                    References Cited

U.S. PATENT DOCUMENTS

| | | | |
|---|---|---|---|
| 2004/0073115 A1* | 4/2004 | Horzewski | A61N 7/00 |
| | | | 600/439 |
| 2008/0167555 A1* | 7/2008 | Qian | A61N 7/02 |
| | | | 600/439 |
| 2011/0130660 A1 | 6/2011 | Cloutier et al. | |
| 2011/0213279 A1 | 9/2011 | Britva et al. | |
| 2015/0157409 A1* | 6/2015 | Onuma | B25J 9/1633 |
| | | | 600/417 |
| 2015/0251016 A1 | 9/2015 | Vo-Dinh et al. | |
| 2016/0228324 A1* | 8/2016 | Garteiser | A61H 23/04 |
| 2022/0370003 A1 | 11/2022 | Rus Calborg et al. | |

OTHER PUBLICATIONS

Lai, Michael, et al., "Introduction to Continuum Mechanics", Butterworth-Heinemann is an Imprint of Elsevier, 2010, pp. 1-535.
Oliver, X., et al., "Continuum Mechanics for Engineers. Theory and Problems", 2nd Edition, Mar. 2017, pp. 1-550.
Dizeux, Alexandre, et al., "Complementarity of Shear Wave Elastography and Dynamic Contrast-Enhanced Ultrasound to Discriminate Tumor Modifications During Antiangiogenic and Cytotoxic Therapy", IEEE International Ultrasonics Symposium Proceedings, Sep. 2014, pp. 1144-1147.

* cited by examiner

Effect vs Acceleration

Repetition 1

Repetition 2

MEDICAL APPARATUS FOR THE NON-INVASIVE TRANSMISSION OF FOCUSED SHEAR WAVES TO IMPACT CELLULAR BEHAVIOUR

FIELD OF THE INVENTION

The present invention refers to a medical apparatus that allows to generate, non-invasively and at a requested depth, shear or compressional waves of controlled frequency and amplitude. The purpose is to impact via mechanotransduction on cellular behaviour, i.e. cell proliferation and cell migration. The aim is to aide classical tumor therapy for instance by rendering cells more receptive to drugs, or by gaining time during chemotherapy by reducing cell migration and hence slowing down the metastatic process.

BACKGROUND OF THE INVENTION

The fact that tumors are often stiffer than the surrounding uninvolved tissue has been known for as long as the disease has been identified. The rigid nature of tumors is the basis for using palpation as a diagnostic method in soft tissues like breast and abdomen, and more recently, as the basis for high-resolution detection of small lesions by MRI elastography or ultrasound. These clinical observations, together with in vitro experiments which demonstrate that stiffness-sensing by cancer and stromal cells influence cell survival and proliferation, opened the door for many investigations that employ novel biocompatible materials with tunable viscoelastic properties. These in vitro systems have the potential to elucidate the mechanical and molecular mechanisms by which cells detect changes in their environment and transduce physical signals to the biochemical signals that control their function, biochemistry, and gene expression.

Mechanotransduction of physical cues to initiate intracellular signaling pathways has recently been documented in many cancer types and a wide range of effects have been observed, ranging from acute changes such as activation of ion channels or protein kinases to long-term changes in cell phenotype that require initiation of gene transcription and protein production.

In the present invention we provide the use of medical apparatus that allows to generate, non-invasively and at a requested depth, shear or compressional waves of controlled frequency and amplitude with the purpose to impact via mechanotransduction on cellular behavior, i.e. cell proliferation and cell migration and thus to treat tumors.

DESCRIPTION OF THE INVENTION

Definitions

Figure 1:
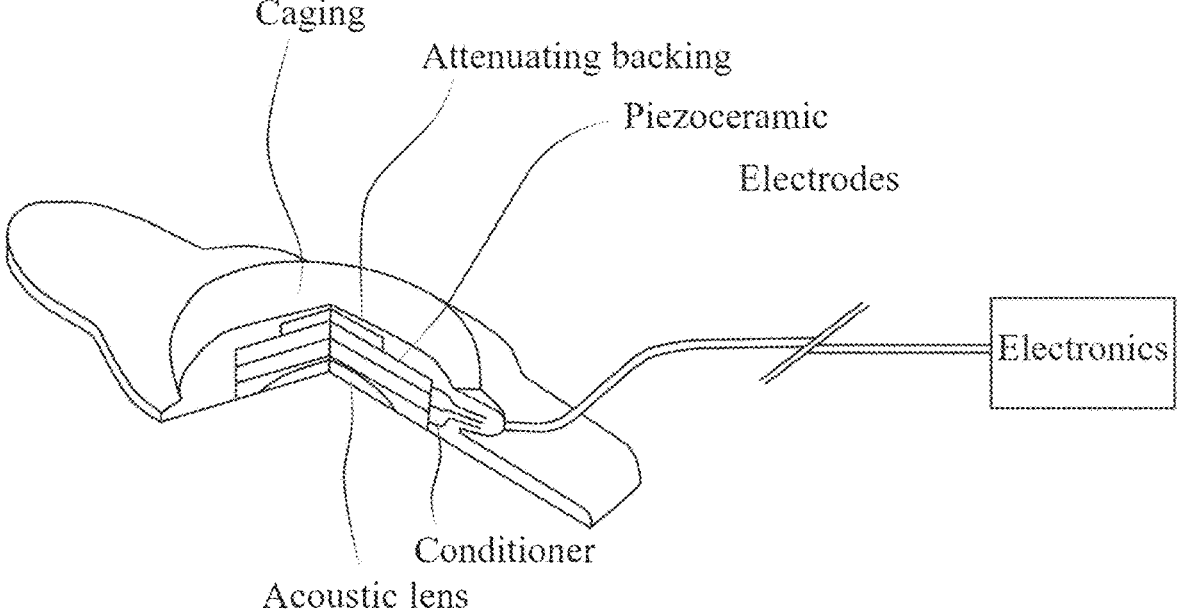
FIG. 1. Illustration of possible design of the medical apparatus that generates compressional waves for tumor co-therapy, which comprises a casing, conditioner and external electronics, as well as the wave generating piezoelectric with electrodes, attenuating backing and acoustic lens in contact with the patient's body.
Figure 2:
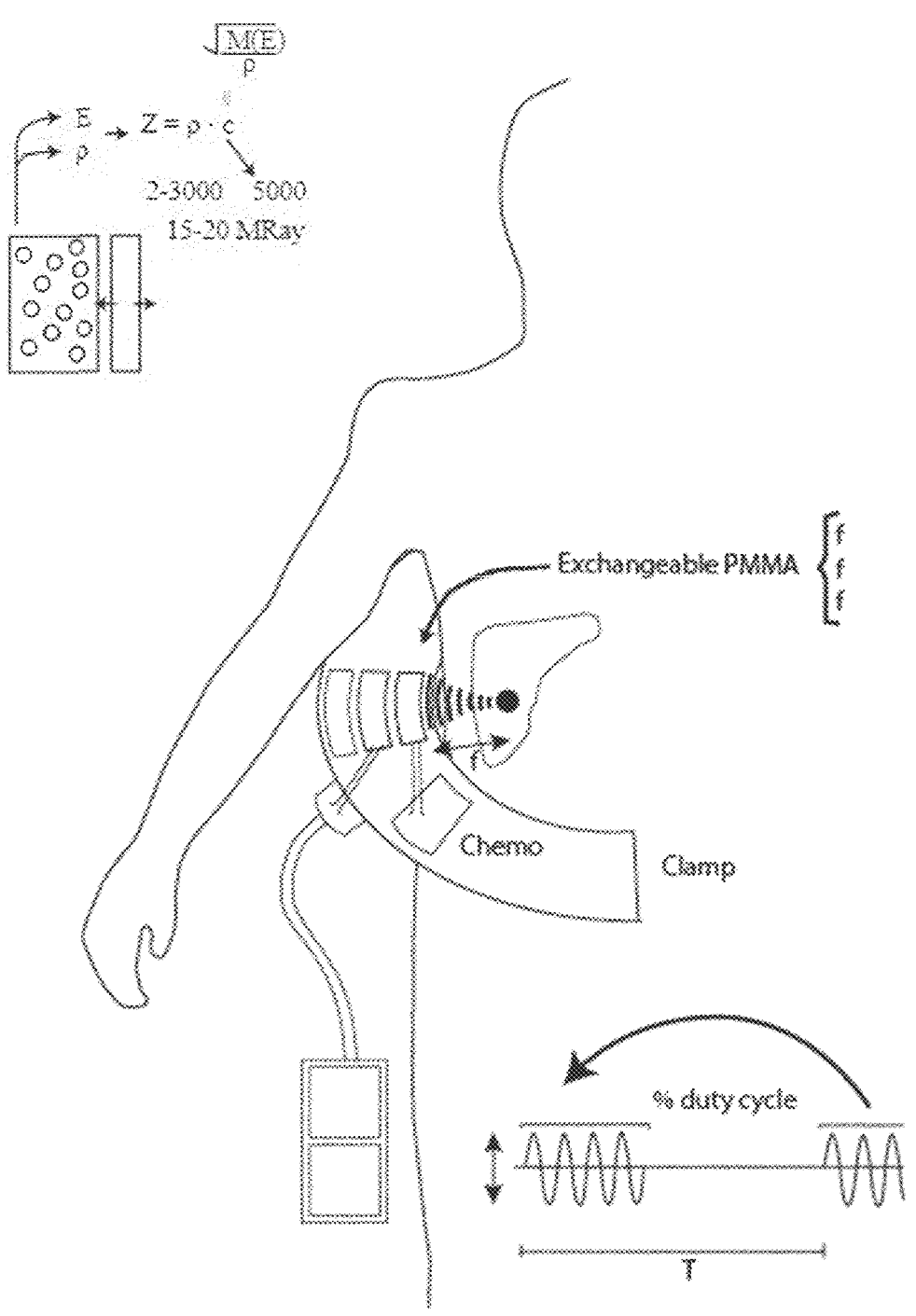
FIG. 2. Illustration of possible design and application of the medical apparatus that generates compressional waves transmitted and focused at tumor for co-therapy, which comprises a casing and holder, conditioner and external electronics, as well as the wave generating piezoelectric with electrodes, attenuating backing and acoustic lens in contact with the patient's body.

In the context of the present invention, "axisymmetric shear waves" is understood as a mechanical shear wave propagated in quasi-incomprehensible media, preferably biological tissues, governed by the elasticity-deflecting component and propagating at shear-wave velocity, in both radial and axial directions, according to the mathematical model in first approximation described below.

The equations that describe the propagation of the axisymmetric wave, as well as the angular oscillatory displacement suffered by the particles of the medium at the passage of the wave can be described by the equations of conservation of the amount of motion, of equilibrium between deformations and displacements, and finally mechanical constituents of the medium of propagation. This last group of equations describes how the propagation medium responds in terms of deformation when subjected to stress, numerous constitutive models have been proposed.
Conservation of the Amount of Movement:

$$\frac{\partial^2 u_\theta}{\partial t^2} = \frac{1}{\rho}\left(\frac{\partial \sigma_{r\theta}}{\partial r} + \frac{\partial \sigma_{\theta z}}{\partial z} + \frac{2}{r}\sigma_{r\theta}\right)$$

Where uθ is the angular displacement of the particles, p is the density of the propagation medium, t it's the time, σrθ y σθz are the shear stresses, r is the radial coordinate and z is the axial coordinate.

In the present invention, the term "Duty Cycle Modulation (DCM)" is understood as switching the signal transmission on an off in a periodic manner defined by the duty cycle defined as the ratio between the pulse duration, or pulse width and the period of a rectangular waveform that multiplies the original signal.

The invention provides for a medical apparatus, a computer program product and a method in the independent claims. Embodiments are given in the dependent claims. As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. 'Computer memory' or 'memory' is an example of a computer-readable storage medium.

Computer memory is any memory which is directly accessible to a processor. 'Computer storage' or 'storage' is a further example of a computer-readable storage medium. Computer storage is any non-volatile computer-readable storage medium. In some embodiments, computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two- or three-dimensional visualization of anatomic data contained within the magnetic resonance imaging data. This visualization can be performed using a computer.

Acoustic radiation force (ARF) is a physical phenomenon resulting from the interaction of an ultrasonic or acoustic wave with the medium where it propagates. The magnitude of the force exerted by an acoustic plane wave at any given location can be calculated as:

$$|F| = \frac{2\alpha I}{c}$$

where
  F is the force in $kg/(s^2\ cm^2)$,
  $\alpha$ is the absorption coefficient in Np/cm,
  I is the temporal average intensity of the ultrasonic wave at the given location in $W/cm^2$, and
  c is the speed of sound in the medium in cm/s.

DESCRIPTION

The present invention provides different devices that enable a precise transmission of shear waves via the surface of a patient to a target region characterized by comprising cancer cells, which is located at a specific depth underneath the skin. Transmission is easiest when tumors are superficial (like for instance for skin cancer), but still feasible for more profound lesions as for instance liver tumors.

In the present invention and as illustrated in the accompanying examples, we propose two ways of generating shear waves at a distance from the body surface:

First, torsional shear waves, preferably axisymmetric shear waves, generated by a ring-like structure that oscillates at a specific frequency on the surface.

Second, shear waves generated via acoustic radiation force that is created by focused ultrasound.

Thus, a first aspect the invention provides for a medical apparatus for treating cancer cells of a subject comprising at least one transducer with a vibrating surface that generates shear waves, wherein the transducer further comprises an applicator for attaching the vibrating surface to an outer surface of the subject, wherein the transducer is operable to vibrate at a frequency between 5 Hz and 2000 Hz, generating shear waves having an amplitude between 0.001 and 50 milliradians, and wherein the medical apparatus further comprises a controller for controlling the vibration of the transducer, wherein the controller is operable for causing the transducer to vibrate for greater than a predetermined period of time for treating the cancer cells, wherein the predetermined period of time is greater than one hour.

The controller is thus operable for causing the transducer to vibrate for greater than a predetermined period of time. The predetermined period of time is greater than one hour for treating the cells. In some examples the cells could be differentiated cancer cells or Cancer Stem cells (CSCs). In some instances, treating the cells may result in cell death. Exposing cells to low frequency, low intensity and long duration shear waves may induce cell death by apoptosis. In general cells of many types are able to sense mechanical status of their micro-environment by a range of processes grouped under the term mechanotransduction. One known effect caused by mechanotransduction is a programmed cell death or apoptosis. This may have a variety of uses. One would be the treatment of cancer cells to kill them through the process of apoptosis.

In this embodiment the predetermined time is determined to be greater than one hour, preferably greater than 1.5 hrs, 2 hrs, 3 hrs, 4 hrs, 6 hrs, 12 hrs or 24 hrs. The predetermined period of time may be broken into a number of sub-chunks of time or intervals such that the bind duration is the predetermined of time. If there are pauses of time that are on the same order as the predetermined period of time then the mechanotransduction process induced in the cells is unchanged. In one example treating the cells may refer to causing or inducing apoptosis in the cells. In another example the term 'treating cells' may refer to causing a mechanotransduction effect in the cells.

In one example the vibrating surface for each of the transducers is less than 42 cm. In one example the transducer is vibrated such that it generates a shear strain value of at least 0.1% within a portion of the subject.

In a preferred embodiment of the first aspect of the invention, the shear waves are axisymmetric shear waves.

In another preferred embodiment of the first aspect of the invention, the medical apparatus comprises a transducer operable to vibrate at a frequency between 5 Hz and 100 Hz, preferably about 10 Hz, generating shear waves, preferably axisymmetric shear waves, having an amplitude between 1 and 20 milliradians, preferably between 5 and 15 milliradians, with a continuous Duty Cycle Modulation (DCM) (100% duty cycle) or with a DCM between 10 and 50% duty cycle, about 50%, and with a repetition period of about 1 s. Such medical apparatus having a transducer operable to vibrate at such parameters, is especially useful in a method of treatment of tumors present from 1 to 10 cm deep from the surface of the skin, such as liver, breast, lung, pancreas, colorectal, prostate, kidney, lymphoma, or thyroid cancer to name a few.

In another preferred embodiment of the first aspect of the invention, the medical apparatus comprises a transducer operable to vibrate at a frequency between 50 Hz and 200 Hz, preferably about 100 Hz, generating shear waves, preferably axisymmetric shear waves, having an amplitude between 0.5 and 5 milliradians, about 1 milliradians, with a continuous DCM (100% duty cycle) or with a DCM between 10 and 50% duty cycle, about 50%, and with a repetition period of about 1 s. Such medical apparatus having a transducer operable to vibrate at such parameters, is especially useful in a method of treatment of tumors present at less than 1 cm deep from the surface of the skin, such as skin tumors as basal cell carcinoma (BCC), squamous cell carcinoma (SCC), melanoma or Paget's disease of the breast.

In another preferred embodiment of the first aspect of the invention, the medical apparatus comprises a transducer which is an electromagnetically driven transducer, wherein preferably the transducer comprises a vibrating surface which in turn comprises a disc or ring-shaped element attached to an electromagnetic device that converts electrical signals into rotational motion. Electromagnetically driven transducers as used herein encompass transducers which have a coil that interacts with the magnetic field of a magnetic resonance imaging system to provide for actuation or the vibration of the vibrating surface. Preferably but not limited to, an electromechanical particularly a miniaturized electromechanical induction motor, on whose axis, a disc is placed that contacts with the patients' tissue to induce an oscillating torque that generates the axisymmetric shear waves propagating into the tissue, preferably encapsulated in a casing with shear wave dampers between the motor and the casing, and any kind of strap for attachment to the patient.

In another preferred embodiment of the first aspect of the invention, the transducer further comprises an applicator for attaching the vibrating surface to an outer surface of a subject, preferably a human subject having a tumor or a cancer disease. The applicator may for instance be an adhesive or band or strap for attaching the transducer to the outer surface of the subject. In another embodiment the at least one transducer is multiple transducers. The controller is operable for controlling the vibrational phase and/or the amplitude of each of the multiple transducers. The controller comprises a processor.

It is noted that the medical apparatus as defined in the first aspect of the invention or in any of its preferred embodiments, may be characterized by further comprising or not an imaging equipment. In particular, in a preferred embodiment of the invention, the medical apparatus as defined in the first aspect of the invention or in any of its preferred embodiments, is characterized by not comprising an imaging equipment. In this embodiment, the applicator is operable for attaching the vibrating surface to skin. Preferably, the vibrating surface shall have a surface area of less than 0.25 cm². This embodiment may be beneficial because it may enable a dermatologist, general practitioner or other healthcare provider to effectively treat cells on the skin or near the skin of a subject (such as a skin cancer) or deep within the skin of a subject (such as a liver cancer). For instance, a melanoma may be visible to the eye. The healthcare provider may be able to place a single transducer over the desired cells or melanoma and effectively treat the cells within a normal office without the need of any imaging equipment.

In another preferred embodiment, the medical apparatus as defined in the first aspect of the invention or in any of its preferred embodiments, might optionally comprise a magnetic resonance imaging system for measuring magnetic resonance data from the subject within an imaging zone. A single transducer or multiple transducers might operable be placed within the imaging zone. During operation they might be placed within the imaging zone or adjacent to the imaging zone such that the regions of the subject vibrated by the multiple transducers are within the imaging zone. The medical apparatus might further comprise a memory for storing machine-executable instructions and a first pulse sequence.

A pulse sequence as used herein is a specification or instructions on how to operate a magnetic resonance imaging system to acquire magnetic resonance data. The use of a particular pulse sequence determines the method for which the magnetic resonance data is acquired. The first pulse sequence is a motion sensitive pulse sequence. A motion sensitive pulse sequence as used herein encompasses a pulse sequence that is able to detect the motion of the subject internally. Examples of a motion sensitive pulse sequence are pulse sequences that perform flow encoding, that are able to measure diffusion, and elastographic pulse sequences. In magnetic resonance elastography the local shear strain can be measured in addition to the stiffness of the subject's tissue. The combination of magnetic resonance elastography and the application of shear waves using single or multiple transducers enables to actually measure the local degree of induced shear forces and properly steer the therapy.

Execution of the machine-executable instructions causes the processor to receive target data descriptive of a location of a target zone within the subject. For instance, the target data may be contained within a treatment plan or may be entered into a user interface by a physician or operator of the medical apparatus. Execution of the instructions further causes the processor to individually vibrate each of the multiple transducers using the controller. Execution of the instructions further causes the processor to acquire first magnetic resonance data during the vibration of each of the multiple transducers using the first pulse sequence. First magnetic resonance data as used here encompasses magnetic resonance data. That is to say the processor uses the pulse sequence to control the magnetic resonance imaging system to acquire the first magnetic resonance data.

Execution of the instructions further causes the processor to calculate a vibration map for each of the multiple transducers using the first magnetic resonance data. The vibration map is descriptive of the shear strain value of vibrations within the subject caused by each of the multiple transducers. The multiple transducers are on the surface of the subject.

The vibration map may also be descriptive of the phase of vibrations caused by each of the multiple transducers within the subject. Execution of the instructions further causes the processor to calculate transducer control data to control the multiple transducers to cause a shear strain value of at least a first predetermined value within at least part of the target zone and less than a second predetermined value outside of the target zone using the vibration map for each of the multiple transducers.

Execution of the instructions may further cause the processor to control the single or multiple transducers with the transducer control data using the controller. In this embodiment the phase and the shear strain value of individual transducers or groups of transducers is measured. Once these vibration maps are acquired it is straight forward to modify the amplitude and/or phase of vibrations caused by the multiple transducers, within the ranges already provided in the first aspect or in any of its preferred embodiments, such that the shear strain value within the target zone is above the first predetermined value and the shear strain value outside of the target zone is below a second predetermined value. This may be advantageous because it enables the causing of mechanotransduction effects for cells within the target zone while leaving cells outside of the target zone unaffected. In one example the first predetermined value is 0.1% or larger. In another example the second predetermined value is 0.05% or less. In one example the frequency of all of the multiple transducers is the same. In another example the frequency of the multiple transducers is also controllable. For instance, the frequency applied to the transducers may be used to control how deeply the shear waves propagate into the body of a subject. By choosing an appropriate vibration frequency it may also help to control the location of the target zone.

In another embodiment execution of the machine-executable instructions might further causes the processor to acquire further magnetic resonance data during control of the multiple transducers with the transducer control data using the magnetic resonance imaging system. The acquisition of the further magnetic resonance data is performed using the first pulse sequence. Further magnetic resonance data as used here encompasses magnetic resonance data. Execution of the instructions further causes the processor to calculate a further vibration map using the further magnetic resonance data. Execution of the instructions further causes the processor to halt vibration of the multiple transducers if the shear strain value is not at least above the first predetermined value within at least part of the target zone and/or is greater than the second predetermined value outside the target zone.

The application of the long duration shear waves by the transducers is performed for a long time predetermined period. During this time, it is possible to make further magnetic resonance measurements to ensure that the shear strain value induced by the multiple transducers is sufficiently high in the target zone to induce a mechanotransduction effect and sufficiently low outside of the target zone to avoid inducing a mechanotransduction effect. This may be performed in several ways. For instance, it may be performed immediately after starting the control of the single or multiple transducers using the controller or it may also be performed repeatedly during the control of the multiple transducers with the transducer control data. For instance, a subject may move or have internal motion which shifts the position of the vibrations caused by each of the multiple transducers within the subject. This example may also involve modifying the transducer control data to correct for internal or external motion of the subject. This embodiment may be beneficial because it more accurately ensures that the shear strain value is above the first predetermined value in the target zone and less than the second predetermined value outside of the target zone.

In another embodiment the memory stores a second pulse sequence. The second pulse sequence is a pulse sequence operable for acquiring magnetic resonance imaging data. The second pulse sequence is an imaging pulse sequence. Execution of the machine-executable instructions further causes the processor to acquire image magnetic resonance data of the subject using the magnetic resonance imaging system. This is performed using the second pulse sequence. Image magnetic resonance data as used herein encompasses magnetic resonance data. Execution of the machine-executable instructions further causes the processor to reconstruct an image using the image magnetic resonance data. Execution of the instructions further causes the processor to locate the target zone within the image using an image recognition module. The step of locating the target zone within the image using the image recognition module registers the target data to the medical apparatus. This may enable more accurate targeting of the target zone.

In another embodiment the controller is operable for adjusting the vibration frequency of each of the multiple transducers. Execution of the instructions further causes the processor to repeat the individual vibration of each of the multiple transducers using the controller and acquisition of the multiple transducer frequencies. The vibration map is a multi-frequency vibration map. Calculating the transducer control data comprises selecting the frequency for the multiple transducers. As was mentioned above, the frequency effects the propagation of vibrations within a subject. Adjusting the vibration frequency of the multiple transducers may allow more accurate targeting of the target zone.

In another embodiment the controller is operable for adjusting the vibrational amplitude and phase of each of the multiple transducers. Calculating the transducer control data comprises selecting a vibrational amplitude and phase for each of the multiple transducers. This embodiment again may enable more accurate targeting of the target zone.

In another embodiment the magnetic resonance imaging system comprises a magnet for generating a main magnetic field. The multiple transducers are operable for functioning within and outside of the main magnetic field. This embodiment may be beneficial because it may enable the image to be removed from the magnetic resonance imaging system. This for instance may be advantageous because it may be uneconomical for a hospital to leave a subject within a magnetic resonance imaging system for a period of several hours. Removing the subject enables a higher throughput. A subject could be placed in a magnetic resonance imaging system to determine the transducer control data and then removed once the vibration map is determined. In another example the subject is removed after the further vibration map is determined.

In another embodiment the medical instrument comprises a subject support. The subject support is operable for removing the subject, the controller and the single or multiple transducers from the magnetic resonance imaging system during the predetermined period of time. This is to say that once the transducer control data has been determined it is possible to remove the subject from the magnetic resonance imaging system to enable other subjects to be placed into the same magnetic resonance imaging system during the control of the multiple transducers with the transducer control data using the controller.

In another embodiment the first predetermined value is greater than or equal to any one of the following: 0.1%, 1%, 2% and 5%.

In another embodiment the second predetermined value is less than or equal to 0.5%.

In another aspect the invention provides for a computer program product comprising machine-executable instructions for execution by a controller for controlling the medical apparatus of the first aspect. In case, such medical apparatus comprises a magnetic resonance imaging system, execution of the instructions causes the processor to receive target data descriptive of the location of a target zone within the subject. Execution of the instructions further causes the processor to individually vibrate each of the single or multiple transducers using the controller. Execution of the instructions further causes the processor to acquire first magnetic resonance data during the vibration of each of the multiple transducers using the first pulse sequence. Execution of the instructions further causes the processor to calculate a vibration map for each of the multiple transducers using the first magnetic resonance data. The vibration map is descriptive of the phase and shear strain value of vibrations caused by each of the multiple transducers within the subject. Execution of the instructions further causes the processor to calculate transducer control data to control the multiple transducers to cause a shear strain value of at least a first predetermined value within at least part of the target zone and less than a second predetermined value outside of the target zone using the vibration map for each of the multiple transducers. Execution of the instructions further causes the processor to control the multiple transducers with the transducer control data using the controller. The advantages of this have been previously discussed.

A second aspect of the invention refers to a medical apparatus for treating cancer cells of a subject comprising at least one transducer with a vibrating surface that generates modulated compression ultrasonic waves that in turn generate shear waves by modulation (frequency reduction) and by mode conversion (compression to shear conversion) when interacting with the tissue of a subject, wherein the transducer further comprises an applicator for attaching the vibrating surface to an outer surface of the subject, and wherein the transducer is operable to vibrate at a frequency between 10 kHz and 20 MHz, generating compression ultrasonic waves having an amplitude between 1 kPa and 50 kPa, with a modulation between 1 and 50% duty cycle, and with a repetition period between 1 microsecond and 1 s, and wherein the medical apparatus further comprises a controller for controlling the vibration of the transducer, wherein the controller is operable for causing the transducer to vibrate for greater than a predetermined period of time for treating the cancer cells, wherein the predetermined period of time is greater than one hour.

It is noted that the generation of the shear waves generated by oscillating disc driven by the electromechanical unit and by acoustic radiation force from high frequency compressional focused ultrasound when interacting with the tissue of a subject should have the same parameters as those reflected in the first aspect of the invention.

In a preferred embodiment of the second aspect, the transducer is preferably operable to vibrate at a frequency between 50 kHz and 5 MHz, generating compression ultrasonic waves having an amplitude between 5 kPa and 15 kPa, preferably about 10 kPa, with a modulation between 1 and 50% duty cycle, preferably about 20%, and with a repetition period between 1 millisecond (ms) and 10 ms.

In another preferred embodiment of the second aspect, the transducer comprises a vibrating surface which in turn comprises an ultrasonic wave generator piezoelectric crystal in the shape of a disc or ring.

It is noted that that the medical apparatus as defined in the second aspect of the invention or in any of its preferred embodiments, may be characterized by further comprising or not an imaging equipment as defined and described in the first aspect of the invention, as well as the processor or computer program as also defined therein.

A third aspect of the invention provides for a method of treating cancer cells or tumors, preferably skin cancer such as basal cell carcinoma (BCC), squamous cell carcinoma (SCC) and melanoma or liver cancer, by using the medical apparatus as defined in any of the first or second aspects of the invention or in any of its preferred embodiments.

In a preferred embodiment of the third aspect of the invention, the method is for treating cancer cells or tumors present at less than 5 cm deep from the surface of the skin, such as skin tumors as basal cell carcinoma (BCC), squamous cell carcinoma (SCC) and melanoma, wherein the method comprises using a medical apparatus which comprises at least one transducer operable to vibrate at a frequency between 50 Hz and 200 Hz, preferably about 100 Hz, generating shear waves, preferably axisymmetric shear waves, having an amplitude between 0.5 and 5 milliradians, about 1 milliradians, with a continuous DCM (100% duty cycle) or with a DCM between 10 and 50% duty cycle, about 50%, and with a repetition period of about 1 s. The method comprises the step of applying the at least one transducer to an external surface of the subject. The method further comprises the step of controlling the at least one transducer to vibrate for greater than a predetermined period of time to treat the cells. The predetermined time is greater than 1 hour, preferably greater than 2, 3, 4, 6, 12, or 24 hrs. The advantages of this method have been previously discussed within the context of the medical apparatus. It is understood that one or more of the aforementioned embodiments of the invention may be combined as long as the combined embodiments are not mutually exclusive.

In another preferred embodiment of the third aspect of the invention, the method is for treating cancer cells or tumors present from 1 to 10 cm deep from the surface of the skin, such as liver, breast, lung, pancreas, colorectal, prostate, kidney, lymphoma, or thyroid cancer, by using a medical apparatus comprising a transducer operable to vibrate at a frequency between 5 Hz and 100 Hz, preferably about 10 Hz, generating shear waves, preferably axisymmetric shear waves, having an amplitude between 1 and 20 milliradians, preferably between 5 and 15 milliradians, with a continuous Pulse Width Modulation (DCM) (100% duty cycle) or with a DCM between 10 and 50% duty cycle, about 50%, and with a repetition period of about 1 s. The method comprises the step of applying the at least one transducer to an external surface of the subject. The method further comprises the step of controlling the at least one transducer to vibrate for greater than a predetermined period of time to treat the cells. The predetermined time is greater than 1 hour, preferably greater than 2, 3, 4, 6, 12, or 24 hrs. The advantages of this method have been previously discussed within the context of the medical apparatus. It is understood that one or more of the aforementioned embodiments of the invention may be combined as long as the combined embodiments are not mutually exclusive.

A fourth aspect of the invention refers to a composition for use in a method for treating tumors in a subject in need thereof, wherein the composition comprises for instance trastuzumab, gemcitabine and tamoxifen each used for the different subtypes of breast cancer, or gemcitabine and inhibitors of BRAF such as vemurafenib, dabrafenib, and encorafenib for melanoma, and wherein the composition is administered prior to, simultaneously to or subsequently to the use of a medical apparatus according to any of the first or second aspects of the invention, in a method that comprises the steps of: applying the at least one transducer of the medical apparatus to an external surface of the subject, controlling the at least one transducer to vibrate for greater than a predetermined period of time to treat the tumors, wherein the predetermined time is greater than one hour, preferably greater than 1.5 hours, greater than 2 hours, greater than 2.5 hours, greater than 3 hours, greater than 3.5 hours, or greater than 4, 6, 12 or 24 hours.

A preferred embodiment refers to a composition suitable for use in a method for treating tumors present from 1 to 10 cm deep from the surface of the skin, such as liver, breast, lung, pancreas, colorectal, prostate, kidney, lymphoma, or thyroid cancer, in a subject in need thereof, wherein the composition comprises an anti-cancer agent, in particular a medicament which contains an active ingredient with a cytotoxic effect and which can be administered orally and/or rectally and/or parenterally, such as, but not limited to, for instance trastuzumab, gemcitabine and tamoxifen each used for the different subtypes of breast cancer, or gemcitabine and inhibitors of BRAF such as vemurafenib, dabrafenib, and encorafenib for melanoma; and wherein the composition is administered prior to, simultaneously to or subsequently to the use of a medical apparatus comprising a transducer operable to vibrate at a frequency between 5 Hz and 100 Hz, preferably about 10 Hz, generating shear waves, preferably axisymmetric shear waves, having an amplitude between 1 and 20 milliradians, preferably between 5 and 15 milliradians, with a continuous Pulse Width Modulation (DCM) (100% duty cycle) or with a DCM between 10 and 50% duty cycle, about 50%, and with a repetition period of about 1 s, wherein the method comprises the step of applying the at least one transducer to an external surface of the subject in a method that comprises the steps of: applying the at least one transducer of the medical apparatus to an external surface of the subject so that the transducer generates a therapeutically effective amount of shear waves within the tumor, controlling the at least one transducer to vibrate for greater than a predetermined period of time to treat the tumors, wherein the predetermined time is greater than one hour, preferably greater than 1.5 hours, greater than 2 hours, greater than 2.5 hours, greater than 3 hours, greater than 3.5 hours, or greater than 4, 6, 12 or 24 hours.

Another preferred embodiment refers to a composition suitable for use in a method for treating tumors present at less than 5 cm, preferably less than 1 cm, deep from the surface of the skin, such as skin tumors as basal cell carcinoma (BCC), squamous cell carcinoma (SCC) and melanoma, in a subject in need thereof, wherein the composition comprises an anti-cancer agent, in particular a medicament which contains an active ingredient with a cytotoxic effect and which can be administered orally and/or rectally and/or parenterally, such as, but not limited to, for instance trastuzumab, gemcitabine and tamoxifen each used for the different subtypes of breast cancer, or gemcitabine and inhibitors of BRAF such as vemurafenib, dabrafenib, and encorafenib for melanoma; and wherein the composition is administered prior to, simultaneously to or subsequently to the use of a medical apparatus comprising at least one transducer operable to vibrate at a frequency between 50 Hz and 200 Hz, preferably about 100 Hz, generating shear waves, preferably axisymmetric shear waves, having an amplitude between 0.5 and 5 milliradians, about 1 milliradians, with a continuous DCM (100% duty cycle) or with a DCM between 10 and 50% duty cycle, about 50%, and with a repetition period of about 1 s, wherein the method comprises the steps of: applying the at least one transducer of the medical apparatus to an external surface of the subject so that the transducer generates a therapeutically effective amount of shear waves within the tumor, controlling the at least one transducer to vibrate for greater than a predetermined period of time to treat the tumors, wherein the predetermined time is greater than one hour, preferably greater than 1.5 hours, greater than 2 hours, greater than 2.5 hours, greater than 3 hours, greater than 3.5 hours, or greater than 4, 6, 12 or 24 hours.

The following examples serve to exemplify the present invention but should not limit the same.

EXAMPLES

Example 1: CSC Therapy Using Axisymmetric Shear Waves In Vitro for Effectiveness Illustration

Materials and Methods

A bioreactor was designed and manufactured to apply axisymmetric shear waves with different configurations of controlled amplitude, frequency and modulation in each well, populated with human pancreatic spheroids cultured in a hydrogel, under standard incubation conditions. The bioreactor was manufactured using biocompatible sterile plastics including PMMA, PLA and others, where the axisymmetric shear wave transducers were incorporated in such a configuration that the whole well volume was insonified with a controlled distribution of axisymmetric shear wave validated with independent techniques in our ultrasonics laboratory, and controlled with wave generators controlled in turn by a computer, connected and placed outside the incubator for temperature control. The axisymmetric shear wave transducers consist of a miniaturized electromechanical motor with a disc of biocompatible plastic attached to the axis and in contact with the surface of the hydrogel.

Results

Tumor cell proliferation rates stimulated with different frequencies and amplitudes of torsional waves. Three different frequencies of stimulation were applied uninterruptedly for 3 days: 10 Hz, 100 Hz and 1000 Hz with matching amplitudes (2.5 V, 5 V, 10 V). To facilitate wave dispersal, multicellular spheres of CSCs were soaked in alginate (1.5%). Unstimulated spheres were used as controls.

Figure 3:
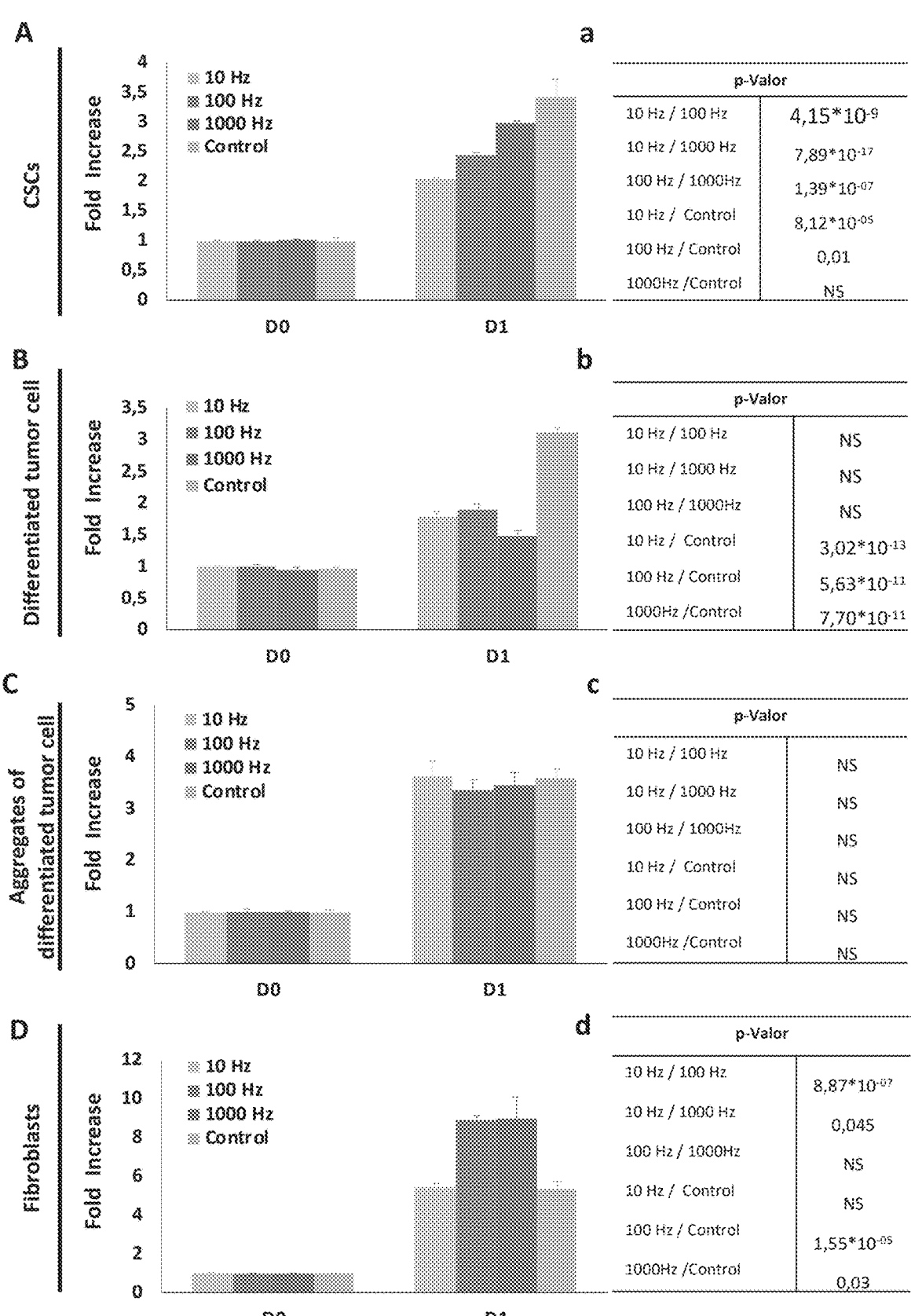
FIG. 3. Proliferation test on different cell types during the first 24 hours of torsional wave stimulation. Fold increase (times that cell proliferation increases with respect to the day of departure) in the cell growth of cancer stem cells (CSC) (A), differentiated melanoma tumor cells (each cell is isolated) (B), differentiated tumor cells where the cells are forming three-dimensional aggregates of similar conformation to the spheres formed by CSCs (C) and fibroblasts forming three-dimensional aggregates of similar conformation to the spheres formed by CSCs (D) at 24 hours. The P values are shown in tables (a), (b), (c) and (d), represented as averages±SEM.
Figure 4:
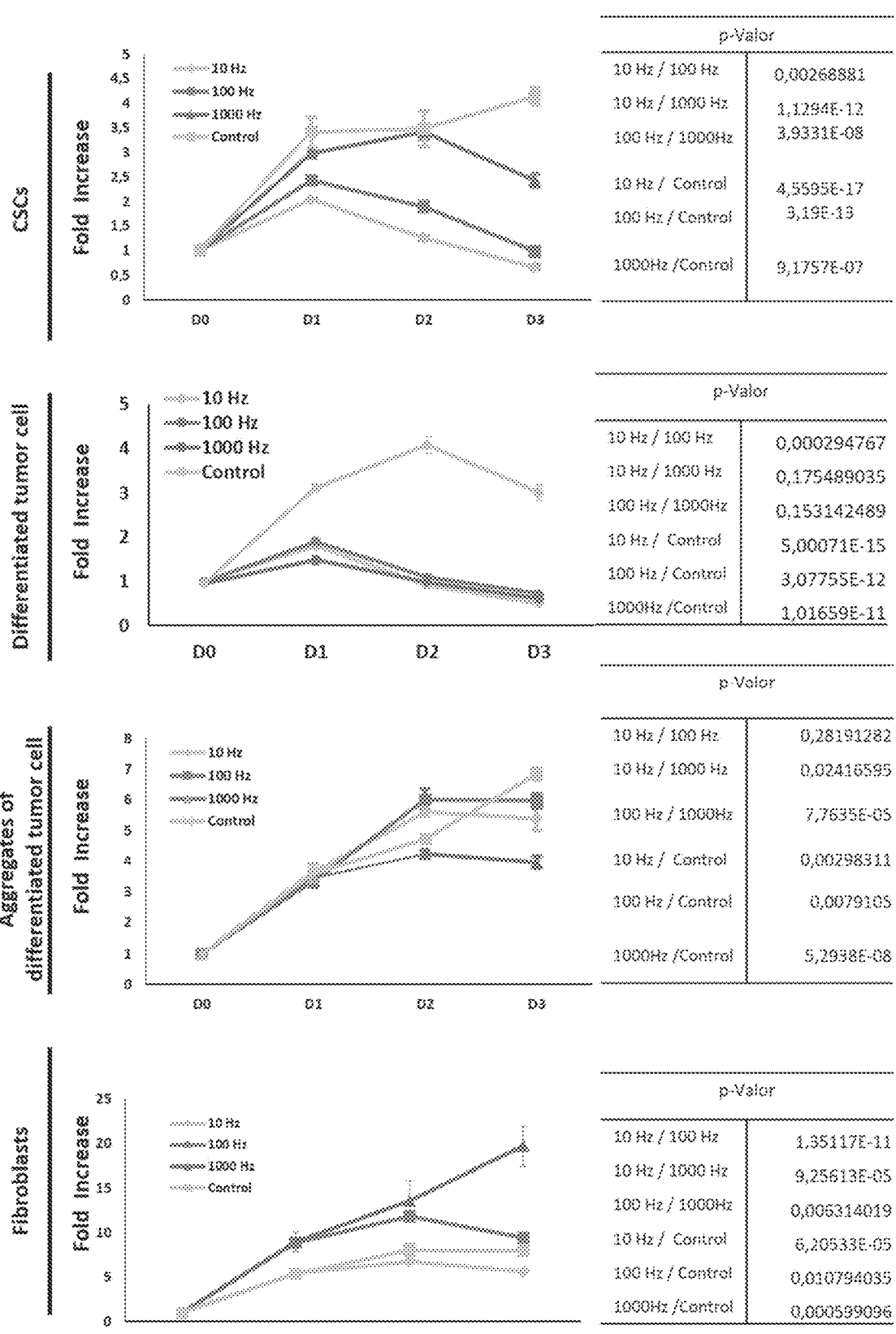
FIG. 4. Proliferation test on different cell types during the first 24 hours of torsional wave stimulation. Fold increase (times that cell proliferation increases with respect to the day of departure) in the growth of cancer stem cells (CSC) (A), differentiated melanoma tumor cells (each cell is isolated) (B), differentiated tumor cells where the cells are forming three-dimensional aggregates of similar conformation to the spheres formed by CSCs (C) and fibroblasts forming three-dimensional aggregates of similar conformation to the spheres formed by CSCs (D) at 72 hours. The normalized values are shown in tables (a), (b), (c) (d), and are plotted as mean±SEM.

As shown in FIG. 3A, all frequencies have an effect on CSC proliferation during the first 24 hours of stimulation. Two of the three frequencies, 10 and 100 Hz, showed significant decreases in growth compared to the control. However, there was no significant difference between 1000 Hz and the control, and the most significant rate of proliferation appeared at the lowest frequency, 10 Hz. Once it was known what happens after the first 24 h, the experiment was extended to observe proliferation rates with longer wave exposure times. After 72 h (FIG. 4A), the stimulated CSCs began to slow down their growth compared to the control, which still increased their proliferation. The frequency of 10 Hz still presented the most significant differences with the control.

In the case of isolated differentiated tumor cells (not forming spheroids), a trypsinization (WO2016020572A1) was performed to isolate them because they have high surface adhesion. After differential trypsinization, the isolated cells were soaked in alginate (1.5%). The results showed that there is no such noticeable contrast after 24 hours of stimulation (FIG. 3B); all frequencies significantly reduced cell proliferation with respect to the control, but no effect distinguishable by a frequency was observed, since there were no significant differences between them. After 72 hours (FIG. 4B) of stimulation, all frequencies decreased their proliferation rate even below the starting point from which the experiment began. This type of cell was the most affected at 72 h, obtaining very low proliferation rates with large differences between each of the frequencies and the control.

To verify whether the different effect of the waves observed between the secondary spheres of CBC and the isolated differentiated tumor cells is due to the fact that the first form is spheroid and the second as a single cell, the same stimulation was performed on aggregates of differentiated tumor cells. For this purpose, aggregates of differentiated tumor cells were obtained after differential trypsinization after they were cultured in suspension with non-serum medium overnight. Unlike the isolated differentiated tumor cells, no significant differences were observed in the aggregates after 24 hours of stimulation, nor between the different frequencies, regardless of the control (FIG. 3C). After 72 hours (FIG. 4C) of stimulation, all frequencies decrease their rate of proliferation, but not as in the case of isolated differentiated tumor cells; the depletion of proliferation at the frequency of 1000 Hz remains the most significant, but the decrease is not as pronounced as in the case of isolated differentiated tumor cells. These results show that torsional waves have a different effect depending on the type of cell; 10 Hz showed the greatest effect in the case of CBC, and the frequency of 1000 Hz in differentiated tumor cells.

Example 2. Fibroblast Proliferation Rates at Different Frequencies and Torsional Wave Amplitudes

Materials and Methods

The bioreactor comprising axisymmetric shear waves and incubator described above was used to culture fibroblasts to validate the absence of adverse effects of the waves on healthy tissue.
Results
It has been observed that the frequency of the torsional waves affects proliferation rates differently depending on the type of cell stimulated. Therefore, the effect of the waves was tested on non-tumor cells such as fibroblasts. First, the fibroblast culture was optimized to form spheroids. Once this goal was achieved, we proceeded in the same way as with tumor cells.

The fibroblast spheres showed a particular behavior. After the first 24 hours of stimulation, proliferation was higher than the other cell types (FIG. 3D. The frequency of 10 Hz did not affect proliferation and its rate of proliferation was similar to the control without significant differences. However, proliferation at frequencies of 100 and 1000 Hz was almost double, and no significant differences were found between them, but with respect to the control and 10 Hz. At 72 hours (FIG. 4D, the trend is similar, with the 10 Hz frequency still showing the least growth, as there are significant differences with respect to the control. Finally, the frequency of 1000 Hz presents the greatest growth. This cell type was the only one in which the stimulation made them grow even more than the control, suggesting that the torsional waves affected differently according to the cell type and that only in healthy cells did they induce a greater increase in proliferation.

Example 3. Alternative Shear Waves Producing Compatible Results

Materials and Methods

Figure 5:
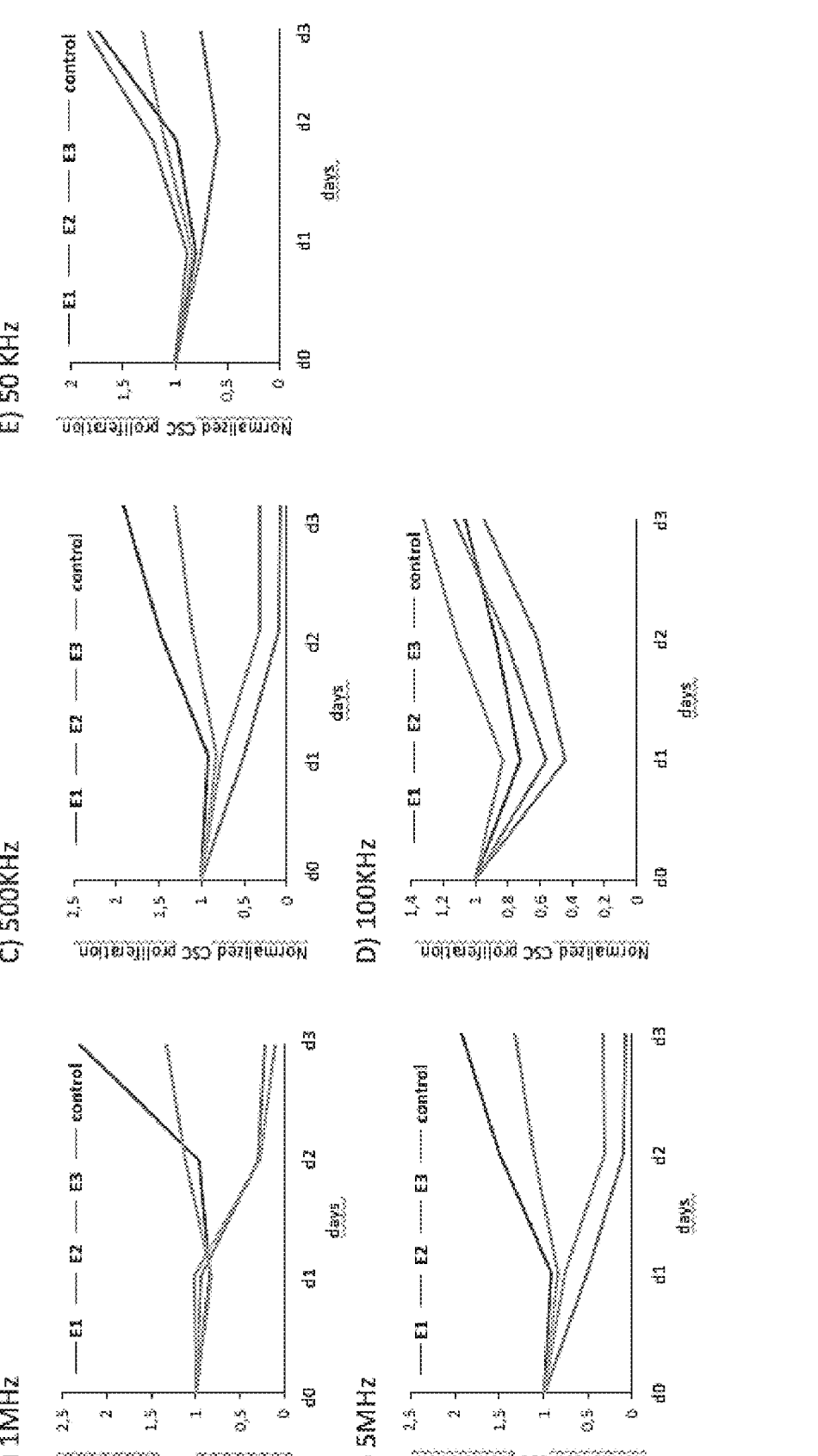
FIG. 5. Therapeutic effect of compressional low intensity ultrasound on human CSC. Initial evidence for the effectiveness of the approach has been collected for isolated cancer stem cells (CSC). Different CSC proliferation effects are shown depending on the combination of ultrasonic frequency (from 50 kHz to 5 MHz, FIGS. 5A to 5E), to energy or amplitude (where control is zero energy, and the increasing levels of ultrasound energy are E1, E2 and E3 respectively) versus CSC culture time (days D0, D1, D2, D3).

An alternative procedure of generating shear waves in cancer was developed consisting of an oscillator applied to a designed bioreactor in order to generate standing shear waves of controlled amplitude and frequency.
Results
Initial evidence for the effectiveness of the approach has been collected for isolated cancer stem cells (CSC). Compared to the control sample, which demonstrates significant growth over three days relative to DO, CSC samples exposed to different amount of shear at different frequencies do show significant reduction in proliferation (FIG. 5).

Figure 6:
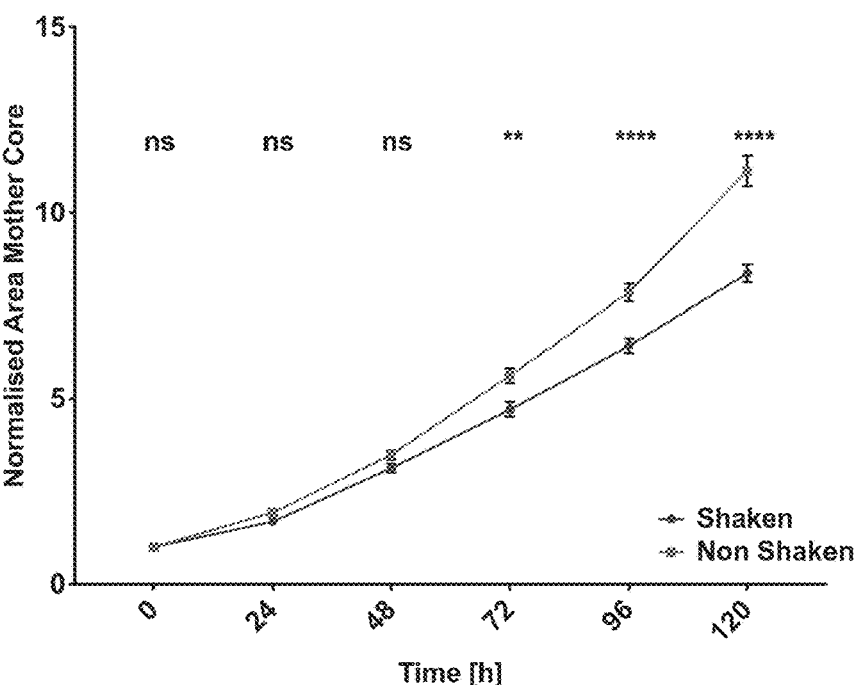
FIG. 6. Proliferation test with 10 Hz shear waves vs control where shear waves have been produced with an alternative technique, using an oscillator capable of generate standing waves in a well, on a different cancer type.

This behaviour is also seen for tumor spheroids that got exposed to about 120 mG of acceleration (0.9% max shear strain). A marked and significant reduction of cell proliferation is recorded after 120 h, with significant changes already noticeable as early as after 72 h (see FIG. 6).

Figure 7:
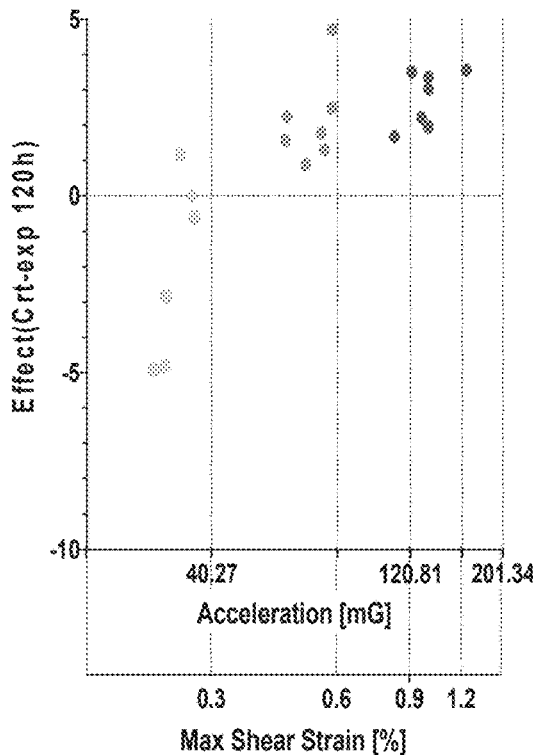
FIG. 7. Effect of the amplitude or energy of the shear waves on the Calreticulin expression: the level of shear at a given frequency does impact the cellular response. While large (~0.9% max shear strain) and intermediate (0.6%) forces reduce cell proliferation, smaller values (~0.3%) do stimulate cell proliferation.

Importantly, we found that the level of shear at a given frequency does impact the cellular response. While large (~0.9% max shear strain) and intermediate (0.6%) forces reduce cell proliferation, smaller values (~0.3%) do stimulate cell proliferation (see FIG. 7)

Example 4: Therapeutic Effect of Compressional Low Intensity Ultrasound on Human CSC In Vitro

Material and Methods

A bioreactor was designed and manufactured to apply compressional wave ultrasound with different configurations of controlled amplitude, frequency and modulation in each well, populated with human pancreatic spheroids cultured in a hydrogel, under incubation conditions. The bioreactor was manufactured using biocompatible sterile plastics including PMMA, PLA and others, where the compressional ultrasonic wave transducers were incorporated in such a configuration that the whole well volume was insonified with a controlled distribution of commercial compressional ultrasonic wave validated with a hydrophone in our ultrasonics laboratory, and controlled with wave generators and power amplifiers controlled in turn by a computer, connected and placed outside the incubator for temperature control.
Results
Initial evidence for the effectiveness of the approach has been collected for isolated cancer stem cells (CSC). Different effects are shown depending on the combination of frequency, amplitude and type of CSC.

Example 5

In this example, we show two phases of the experimental support that warrant our concept of mechanotherapy with torsional or axisymmetrical waves (shear waves that propagate in depth and radially minimizing spurious compressional wave components, whose propagation obey Reissner-

17

18

Figure 8:
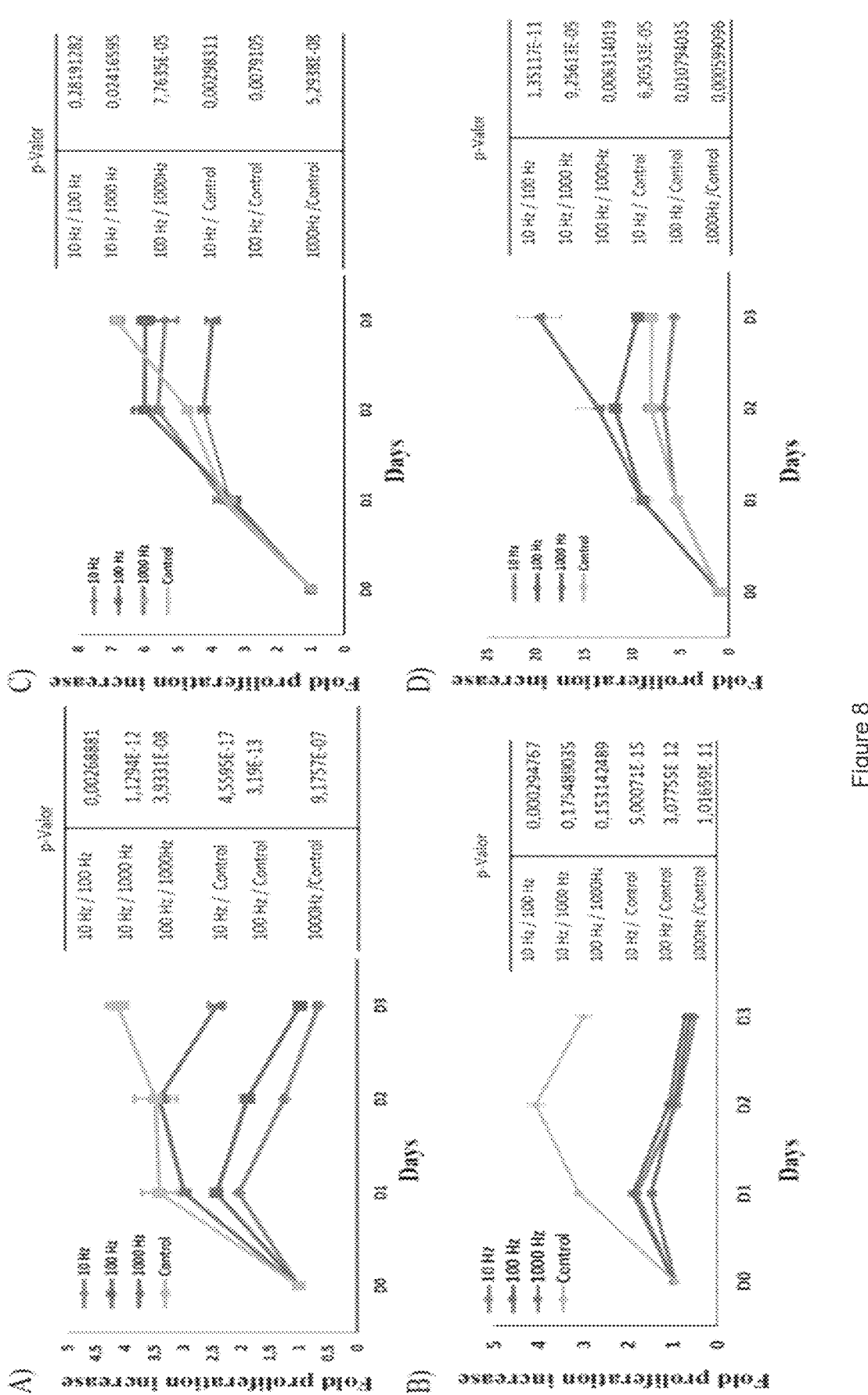
FIG. 8. Preliminary evidence of mechanotherapy in different cell cultures after 72 h. (A) The frequency of 10 Hz presented the most significant differences with the control for cancer stem cells (CSCs) but all slowed down their growth compared to the control. (B) differentiated tumor cells decreased proliferation rate for all frequencies of cells not only below control but below day 0. (C) Fibroblasts behaved differently: stimulation made them grow more than the control, suggesting different torsional wave effect depending to the cell type, and suggesting that the impact was positive in healthy cells.

Sagoci equations): our currently ongoing experiments evidence that some frequencies and energies of torsionally-configured shear waves strongly reduce proliferation rates of multicellular human tumoroids in cultures. Notwithstanding, we observed that the frequency of the torsional waves affects proliferation rates differently depending on the type of cell stimulated (see FIG. 8).

Figure 9:
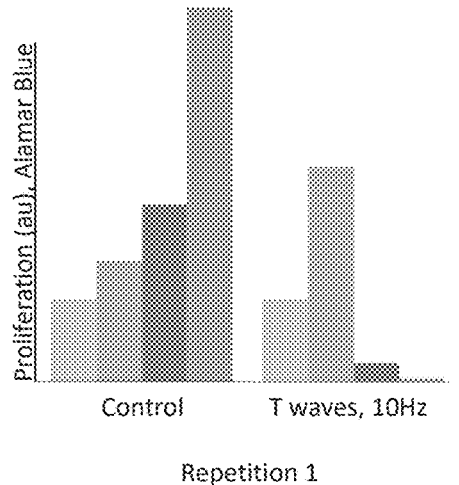
FIG. 9. Proliferation rates over the first week of T-wave therapy at 10 Hz compared to control, in MEL-1 3D CSC cultured in alginate hydrogel.
Figure 9:
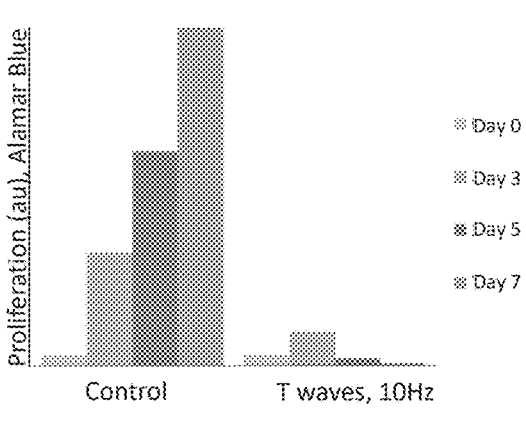

The second phase of experimental support extends to 7 days the experiments, and optimizes the frequency and energy at 10 Hz and exhibits a clear effect of the therapy (T-waves) in comparison with untreated control (FIG. 9), which appears robust during the 2 repetitions performed so far.

The invention claimed is:

1. A medical apparatus suitable for treating cancer cells of a subject comprising at least one transducer with a vibrating surface that generates torsional shear waves and a controller for controlling vibration of the at least one transducer, wherein the at least one transducer further comprises an applicator for attaching the vibrating surface to an outer surface of the subject, wherein the controller is configured to control the at least one transducer to vibrate at a frequency of about 10 Hz, generating torsional shear waves having an amplitude between 1 and 20 milliradians, wherein the controller is operable for causing the at least one transducer to vibrate for greater than a predetermined period of time for treating the cancer cells, wherein the predetermined period of time is greater than one hour, wherein the torsional shear waves are axisymmetric torsional shear waves and wherein the at least one transducer is an electromagnetically driven transducer, wherein the at least one transducer comprises a vibrating surface which in turn comprises a disc or ring-shaped element attached to an electromagnetic device that converts electrical signals into rotational motion, the disc or ring-shaped element configured to oscillate to generate the torsional shear waves.

2. The medical apparatus according to claim 1, wherein the cancer cells are in a tumor 1 cm to 10 cm deep from a skin surface and the controller is configured to control the at least one transducer to vibrate at the frequency of 10 Hz, generating the axisymmetric torsional shear waves, having the amplitude between 5 and 15 milliradians, with a continuous Duty Cycle Modulation (DCM) (100% duty cycle) or with a DCM between 10 and 50% duty cycle, and with a repetition period of 1 s.

3. The medical apparatus according to claim 2, wherein the DCM is 50% duty cycle.

4. The medical apparatus of claim 1, wherein the at least one transducer is one or multiple transducers, wherein the controller is operable for controlling the vibrational phase and/or amplitude of each of the multiple transducers, and wherein the controller comprises a processor.

5. The medical apparatus of claim 1, wherein the at least one transducer is a single transducer or multiple transducers, wherein the applicator is operable for attaching the vibrating surface to skin, and wherein the vibrating surface has a surface area less than 0.25 square centimeters.

6. The medical apparatus of claim 1, wherein the predetermined period of time is selected from the group consisting of greater than 1.5 hours, greater than 2 hours, greater than 2.5 hours, greater than 3 hours, greater than 3.5 hours, and greater than 4 hours.

7. A non-transitory computer-readable medium, the non-transitory computer-readable medium storing a computer program comprising machine executable instructions, which, when executed by a controller, controls a medical apparatus according to claim 1.

\* \* \* \* \*